United States Patent [19]

Jones

[11] Patent Number: 4,942,296
[45] Date of Patent: * Jul. 17, 1990

[54] SUPER-CRITICAL FLUID MASS SPECTROMETER

[75] Inventor: David S. Jones, Sale, England

[73] Assignee: VG Instruments Group Limited, Crawley, England

[*] Notice: The portion of the term of this patent subsequent to Dec. 27, 2005 has been disclaimed.

[21] Appl. No.: 216,092

[22] Filed: Jul. 7, 1988

[30] Foreign Application Priority Data

Jul. 10, 1987 [GB] United Kingdom ............... 8716252

[51] Int. Cl.⁵ ............................................. H01J 49/26
[52] U.S. Cl. ................................... 250/288; 250/282; 250/423 R
[58] Field of Search ............... 250/288, 288 A, 281, 250/282, 423 R

[56] References Cited

U.S. PATENT DOCUMENTS

| | | | |
|---|---|---|---|
| 4,479,380 | 10/1984 | Novotny | 73/61.1 C |
| 4,647,772 | 3/1987 | Lewis | 250/288 A |
| 4,794,252 | 12/1988 | Bateman | 250/281 |

*Primary Examiner*—Bruce C. Anderson
*Attorney, Agent, or Firm*—Chilton, Alix & Van Kirk

[57] ABSTRACT

The invention provides a mass spectrometer for the analysis of a sample dissolved in a super-critical fluid. The fluid is expanded directly into an ionization chamber without a liquid-gas transition and the sample is ionized by means of a glow discharge established in the chamber. Preferably the electrodes between which the discharge is struck comprise the wall of the ionization chamber and the tube through which the super-critical fluid enters the chamber. The spectrometer is primarily intended for use with a super-critical fluid chromatograph.

15 Claims, 3 Drawing Sheets

SUPER-CRITICAL FLUID MASS SPECTROMETER

This invention relates to a mass spectrometer adapted for the analysis of a sample comprising a super-critical fluid, and in particular to a mass spectrometer directly coupled to a super-critical fluid chromatograph.

Combined liquid chromatography - mass spectrometry (LC-MS) is potentially a very powerful technique, but it is limited by the restricted operating conditions imposed by each of the different types of available interfaces. Existing LC-MS interfaces are successful only with particular types of sample or with certain types of solvents, and a completely universal LC-MS interface has not so far been developed.

Super-critical fluid chromatography (SFC) offers a more efficient alternative to liquid-chromatography, and interfaces for directly coupling a super-critical fluid chromatograph and a mass spectrometer have been described in the following references:
  (1) Wright, Kalinoski, et al, J. High Res. Chrom. and Chrom. Commun. 1986, vol. 9 pp 145-153;
  (2) Randall, Wahrhaftig, Rev. Sci. Instrum. 1981 vol 52 (9) pp 1283-1295;
  (3) Smith, Fjeldsted, Lee, J. Chromatogr. 1982 vol 247 pp 231-243;
  (4) Smith, Felix, Fjeldsted, Lee, Anal. Chem. 1982 vol 54 (11) pp 1883-5.

In these prior SFC-MS instruments, at least some of the eluent from the chromatograph is directed into a conventional electron-impact or chemical ionization ion source incorporated in the mass spectrometer. Unfortunately, these ionization techniques are unsuited to many of the biochemicals for which the use of a SFC-MS instrument would provide a convenient alternative to LC-MS.

It is an object of the present invention to provide a mass spectrometer for the analysis of samples dissolved in a super-critical fluid which is capable of ionizing a greater range of compounds than prior instruments.

It is another object of the invention to provide a super-critical fluid chromatograph—mass spectrometer with improved performance in comparison with prior spectrometers.

In accordance with this objective there is provided a mass spectrometer for the analysis of a sample in solution in a super-critical fluid, said spectrometer comprising:
  (a) means for reducing the pressure of said super-critical fluid solution and introducing at least some of the resulting sample-containing expanded fluid into an ionization chamber maintained substantially below atmospheric pressure;
  (b) means for maintaining within said ionization chamber a glow discharge whereby to produce ions characteristic of said sample;
  (c) means for extracting from said ionization chamber at least some of said ions; and
  (d) means for mass analyzing at least some of the said ions extracted by said means for extracting.

In a preferred embodiment a super-critical fluid chromatograph-mass spectrometer is provided by conducting the eluent from a super-critical fluid chromatograph to said means for reducing the pressure.

In a further preferred embodiment the means for reducing the pressure is disposed adjacent to said ionization chamber and comprises a short non-viscous restriction which allows the expansion of the super-critical fluid without an intermediate liquid-gas transition. A suitable restriction may for example comprise a diaphragm containing a small laser drilled orifice (typically having an area between $1 \times 10^{-12}$ and $3 \times 10^{-11}$ $m^2$, i.e, for a circular orifice, approximately 2-5 micron in diameter). It is important that the dead volume between the SFC column and the means for reducing the pressure, and of the means for reducing the pressure itself, is as small as possible if the resolution of the chromatograph is not to be degraded. A short orifice-type restriction is therefore preferred in relation to a long narrow-bore capillary, but the use of such a capillary is not excluded and indeed may have advantages in certain circumstances (see, eg, Chester, Innis and Owens, Anal. Chem. 1985, vol 57 pp 2243-47).

In further preferred embodiments the glow discharge is maintained between at least two electrode means, at least one of which is provided by, or is closely adjacent to, the means for reducing pressure.

According to another aspect the invention provides a method of analyzing a sample in solution in a super-critical fluid, said method comprising the steps of:
  (a) reducing the pressure of said super-critical fluid solution and expanding at least some of said solution into the gas or vapour phase;
  (b) admitting at least some of the resultant sample-containing expanded fluid into an ionization chamber maintained at sub-atmospheric pressure;
  (c) ionizing at least some of said sample by means of a glow discharge established in said ionization chamber to produce ions characteristic of said sample; and
  (d) extracting from said ionization chamber and subsequently mass analyzing at least some of said ions.

Preferably the glow discharge has a cathode dark space into which the super-critical fluid is expanded.

The use of a glow discharge for ionizing the sample permits ionization of high molecular weight and thermally labile biochemicals without the extensive fragmentation which is a feature of the ionization of such samples by means of a conventional electron impact or chemical ionization source. It has also been found that if the super-critical fluid is expanded directly into the cathode dark space of the discharge then a greater range of compounds can be successfully ionized without excessive fragmentation, and a greater range of fluid flow rates and compositions can be used.

Although in many cases, good sensitivity is observed when the glow discharge is struck in the ionization chamber in an atmosphere comprising only the expanded super-critical fluid solution, in other cases advantage may be had by introducing an additional gas into the ionization chamber so that the glow discharge takes place in an atmosphere comprising at least the additional gas. For example, ammonia has been found to be effective in increasing the ionization efficiency of samples of high molecular weight species. The additional gas may conveniently be introduced into the ionization chamber through a separate inlet pipe.

The glow discharge is preferably struck and maintained in the ionization chamber between two electrodes between which a potential difference of approximately 500 V is applied. Typically the pressure in the ionization chamber will be maintained between 1 and 100 mbar and a current of 0.1-10 mA will flow between the electrodes. In a preferred embodiment one of the electrodes comprises the wall of the ionization chamber and the means for reducing the pressure may comprise an electrically conductive nozzle or a diaphragm containing one or more very small holes, which is made the cathode electrode of the discharge, thereby ensuring that the fluid is expanded into the cathode dark space of the discharge. Alternatively, the means for reducing pressure may be made from a quartz, silica or glass capillary tube which is sealed at the end except for one or more small diameter holes typically 1–10 micron diameter. This capillary tube may be inserted axially into a hollow electrically conductive cylinder or tube which forms the cathode electrode. In this way an electrode means is formed adjacent to the orifice(s) and the super-critical fluid is expanded into the cathode dark space. The end of the capillary tube may be additionally metalized in order to provide an electrically conductive surface which can be maintained at the cathode potential, thereby preventing disturbances to the glow discharge by charging which may occur with an untreated surface.

With the latter arrangement, the dead volume between the SFC column and the ionization chamber may be substantially eliminated by making the capillary tube the column itself. The packing material may then extend at least as far as a retaining frit situated inside the tube immediately adjacent to the orifice. Alternatively, a micro-capillary SFC column may be terminated with a small orifice leading into the ionization chamber, resulting in substantially zero dead volume.

Ions may be extracted from the ionization chamber by any suitable method. Typically a sampling cone comprising a hollow conical member with a small hole in its apex is provided, as in a conventional LC-MS "Thermospray" type mass spectrometer. This is typically mounted apex-first and downstream of means for reducing the pressure through the wall of the ionization chamber with its axis (the "first axis") substantially perpendicular to the axis (the "second axis") of the means for reducing the pressure (i.e. the axis along which the fluid is expanded into the chamber). The hole in the cone leads into a second evacuated chamber which contains any suitable mass analyzer (e.g. a quadrupole or a magnetic sector analyzer, as required).

Selection of the distance between the means for reducing the pressure and the sampling cone is important for efficient operation of the spectrometer. It is preferably adjusted to maximize transmission of ions characteristic of the sample from the ionization chamber into the mass analyzer. Conveniently, the distance between the spraying means and the hole in the cone is made adjustable by provision of means for adjusting the length of the pressure reducing means (and/or its connecting capillary) which protrudes into the ionization chamber. Typically a distance of 3–6 mm between the means for reducing the pressure and the hole in the sampling cone (i.e. between the means for reducing the pressure and the "first axis" above referred to) is suitable.

A repeller electrode may be positioned inside the ionization chamber to electrostatically deflect ions formed in the chamber through the hole in the sampling cone.

In the case of a quadrupole mass analyzer, the potential of the walls of the ionization chamber and the sampling cone will be maintained at the ion energy of the mass analyzer which is usually close to ground potential. The anode electrode of the glow discharge preferably comprises the walls of the ionization chamber, so that the cathode electrode will be several hundred volts more negative, typically 500 volts, with respect to ground. A similar arrangement may be adopted for use with a magnetic sector mass analyzer, but in this case the ionization chamber walls (also the anode) will be maintained at the accelerating voltage of the spectrometer, typically +4 to +8 kV with respect to ground.

In order to prevent condensation of the sample or the super-critical fluid into the liquid phase during the pressure reduction step it is preferable to supply heat to the means for reducing pressure and its connecting capillary (if provided). A typical operating temperature for these components may be about 200° C., but this will be dependent on the flow rate and composition of the super-critical fluid.

Dependent also on the composition of the fluid, and on the pumping speed at the ionization chamber, is the flow rate of super-critical fluid which may be introduced into the spectrometer. Typically a column flow rate of 10–100 $\mu l$ min$^{-1}$ can be accepted. Larger flow rates may be used with a splitting type SFC-MS interface, for example as described by Chester, Innis, and Owens (Anal. Chem. 1985 vol 57 pp 2243-) and Randall and Wahrhaftig (Rev. Sci. Instrum., 1981, vol 52 (9) pp 1283–95).

A preferred embodiment of the invention will now be described in greater detail by way of example and by reference to the figures in which.

Figure 1:
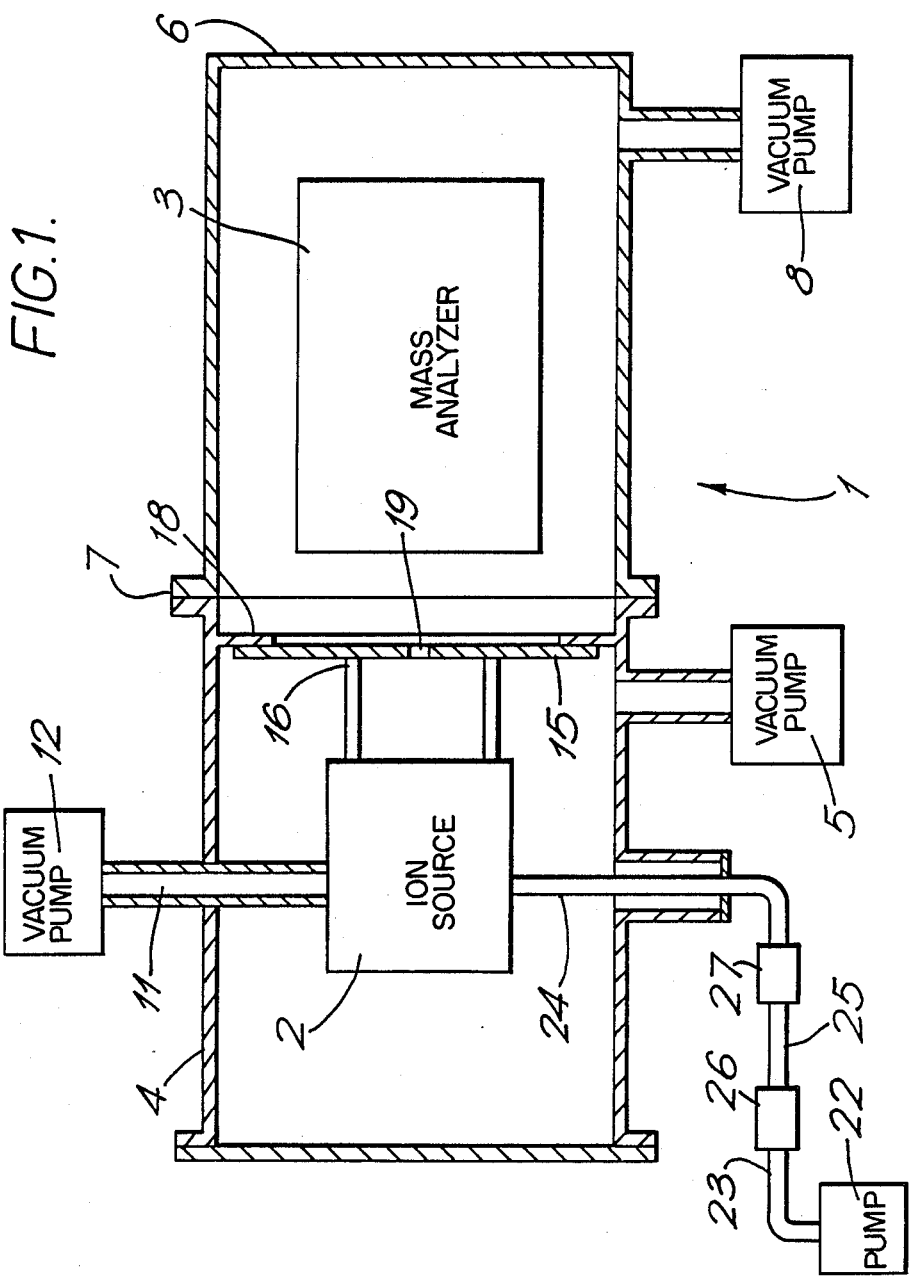
FIG. 1 is a schematic drawing of a mass spectrometer according to the invention.

Referring first to FIG. 1, a mass spectrometer 1 comprises a discharge source 2 and a mass analyzer 3. Source 2 is contained in a housing 4 which is evacuated by a vacuum pump 5, capable of maintaining the pressure in housing 4 below $10^{-3}$ mbar. Analyzer 3 is contained within housing 6 which is attached to housing 4 by a flanged joint 7. A vacuum pump 8 is used to maintain the pressure in housing 6 below $10^{-5}$ mbar. Mass analyzer 3 may comprise any conventional mass analyzer, for example a quadrupole mass analyzer, high or low resolution magnetic sector mass analyzers, a time-of-flight mass analyzer, or an ion-cyclotron resonance spectrometer.

Figure 2:
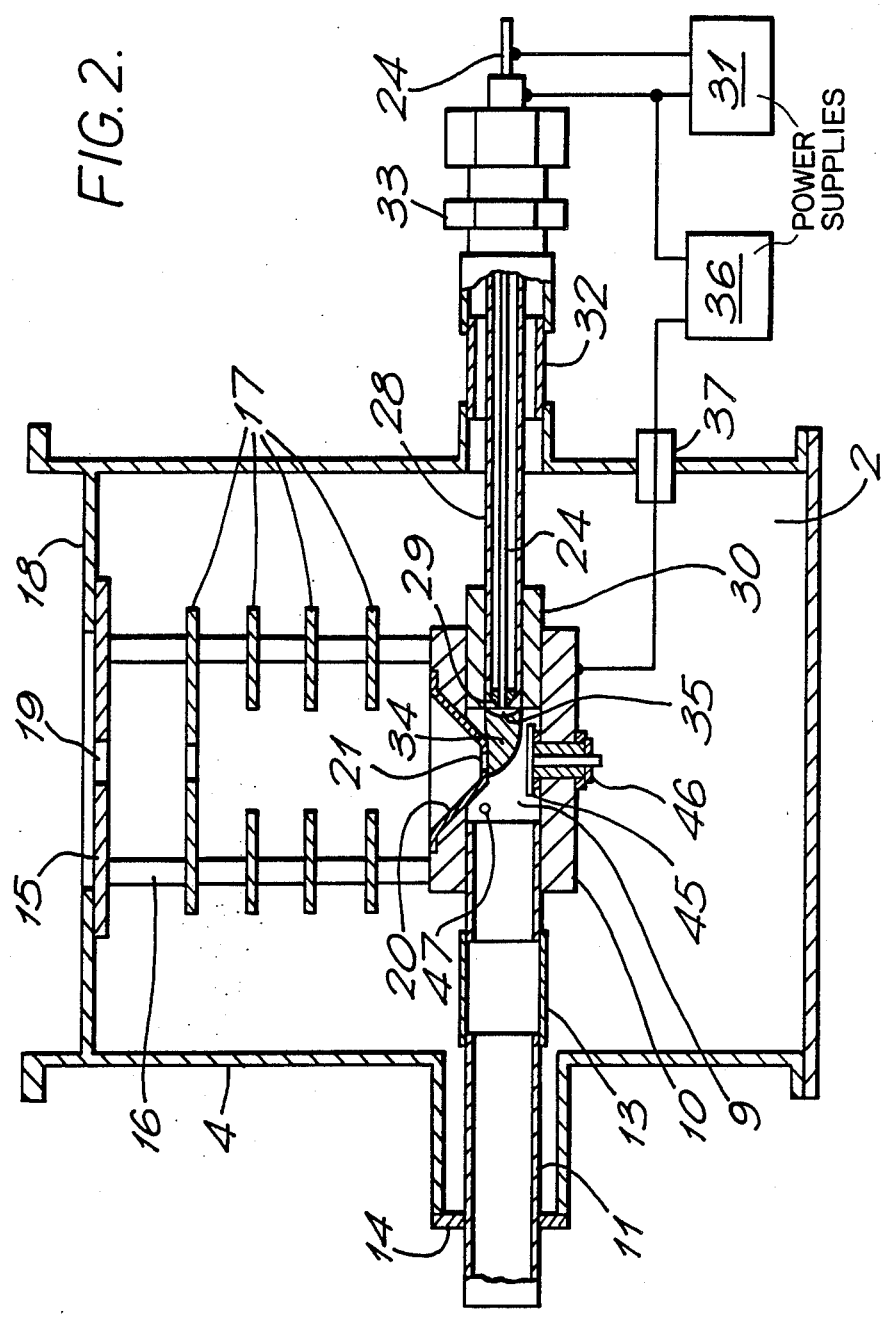
FIG. 2 is a drawing of a discharge ionization source suitable for use in the invention.

A discharge ionization source 2 suitable for use in a spectrometer according to the invention in conjunction with a packed SFC column is shown in greater detail in FIG. 2. It comprises an ionization chamber 9 bounded by a wall and formed in an ionization block 10 which is evacuated through a wide-bore tube 11 by a mechanical vacuum pump 12 (FIG. 1). Pump 12 is of a sufficient capacity to ensure that the pressure inside chamber 9 remains within the desired range during operation. In most cases, the potential of block 10 will not be ground, so that tube 11 also comprises a tubular insulator 13. Typically, tube 11 may be made from a stainless steel tube, about 10 mm diameter, and the insulator 13 may comprise PTFE tube. It is also desirable that a flexible portion is incorporated in tube 13 to allow for slight misalignment of its mounting port 14 on housing 4 and ionization block 10. This is easily achieved when insulator 13 is a short section of PTFE tube. Alternatively, stainless steel tube 11 can be omitted, and insulator 13 can be extended through port 14 to connect directly to pump 12.

If the discharge source 2 is required to be used in conjunction with a capillary SFC column, then, to allow the pressure in the ionization chamber to reach a sufficiently high value for a glow discharge to be established, the wide-bore tube 11 and vacuum pump 12 should be omitted and the ionization chamber 9 completely sealed with the exception of the hole in sampling cone 20 (described in detail below).

The ionization block 10 is supported from a source mounting flange 15 by four source mounting rods 16. Each mounting rod comprises a solid ceramic rod over which a plurality of tubular ceramic spacers are fitted. The focusing and deflecting electrodes 17 are supported on the rods 16 between these spacers.

Source mounting flange 15 is in turn mounted on a flange 18 which is welded to the inside wall of housing 4 and contains a small aperture 19 through which ions formed in source 2 pass into the mass analyzer 3. In the case when analyzer 3 is a magnetic sector analyzer, aperture 19 comprises a small rectangular slit which is typically $0.1 \times 5$ mm. Means, external to housing 4, may be provided for adjusting the width of the slit. In the case when analyzer 3 is a quadrupole analyzer, aperture 19 is typically a small round hole.

A sampling cone 20 comprising a hollow conical member containing in its apex a small aperture 21 (typically 0.3 mm diameter), is fitted so that its apex protrudes through the wall of the ionization chamber 9. Ions formed in chamber 9 leave through aperture 21 and are focused on to the aperture 19 in mounting flange 15 by means of the electrical field created by electrodes 17. These electrodes are connected to suitable electrical supplies by means of feedthrough insulators (not shown) fitted in the wall of housing 4, and operate in a conventional way.

A repeller electrode 45 is fitted inside chamber 9 on an insulated support structure 46. The potential on electrode 45, typically of the same polarity as that of the ions being analyzed, may be adjusted to optimize the transmission of ions into the mass analyzer 3.

The super-critical fluid containing the sample to be analyzed, typically the eluent from a super-critical fluid chromatograph, is pumped by pump means 22 (FIG. 1) through narrow bore tubes 23 and 24 into the discharge ionization source 2. If tubes 23 and 24 are metallic, an insulating tube 25, made typically from quartz, glass or PTFE, may be inserted between the tubes 23 and 24 and connected to them by couplings 26 and 27. This provides electrical insulation between the pump means 22 and the ionization block 10 of discharge source 2 which may be at high potential, especially in the case when analyzer 3 is a magnetic sector analyzer, permitting the pump means 22 to be at ground potential. Typically, pump means 22 is a super-critical fluid chromatograph, and the eluent may typically comprise carbon dioxide at a pressure of 10-50 atmospheres and containing a polar modifier such as methanol. Tubes 23, 24 and 25 should preferably be heated. Electrical heating tape or a simple oven may be conveniently employed. The volume of tubes 23, 24 and 25 should also be kept to a minimum to minimize loss of chromatographic resolution, and generally their internal diameter should not exceed 0.15 mm.

Narrow-bore tube 24 is fitted inside a wide-bore tube 28 which is joined to the end of tube 24 inside chamber 9. Means 29 for reducing the pressure are described in detail below. An electrical insulator 30 seals tube 28 into ionization block 10 and provides electrical insulation between them. Tube 24 is preferably heated by an electrical current passed through it via tube 28 from heater power supply 31. Preferably, narrow-bore tube 24 and the wide-bore tube 28 are made from stainless steel.

Tube 28 is supported by a second electrical insulator 32 fitted in a port on housing 4 and by pipe coupling 33 as shown in FIG. 2. The distance between means 29 for reducing the pressure and aperture 21 in sampling cone 20 is set by loosening the nut on pipe coupling 33 and sliding tube 28 in the coupling until the desired distance is achieved, after which the nut is retightened. To facilitate this, the ferrule in coupling 33 is preferably made from PTFE. For optimum operation, the distance should be set to between 3 and 6 mm.

A glow discharge 34, having a cathode dark space 35, is established between at least two electrode means. As explained, further advantage is gained by making means 29 for reducing the pressure the cathode electrode and this is done in the embodiment shown in FIG. 2. In the FIG. 2 embodiment, a cathode comprising means 29 for reducing the pressure, and an anode comprising the ionization block 10 are provided. A glow discharge power supply 36 generates a suitable potential difference which is applied to the tube 24 (negative) and the ionization block 10 (positive). Ionization block 10 is connected to power supply 36 by means of feedthrough 37 in housing 4. It is also maintained at the accelerating voltage of the mass spectrometer, so that supplies 31 and 36 should be capable of floating at a potential of up to 8 kV above ground if analyzer 3 is a magnetic sector analyzer.

An inlet 47 may be provided in ionization block 10 through which an additional gas can be introduced into ionization chamber 9 typically to improve the efficiency of certain samples by the glow discharge 34.

Typically, the glow discharge power supply 36 is capable of generating a potential of approximately 500 volts at a current of up to 10 mA. The pressure in chamber 9, which is also advantageously heated as it is in a conventional ionization source, may be between 1 and 100 mbar (e.g. of carbon dioxide). A discharge current of 0.1-10 mA is typical. Power supply 36 should preferably be an adjustable voltage type because the potential difference required for optimum operation is dependent on the nature of the SFC eluent and the pressure in chamber 9. The discharge current is adjusted and maintained at a value such that the "normal" glow of the discharge at least partly covers means 29 for reducing the pressure.

Heater power supply 31 is typically capable of delivering up to 20A at a low potential difference so that narrow-bore tube 24 is heated to the temperature required to prevent liquefaction of super-critical fluid. Typically a power of 150 W is suitable, but this will be dependent on the material used for tubes 24 and 28 and on their cross-sectional areas. The temperature required to prevent liquefaction is best selected by experiment. If it is too low, erratic and irreproducible results are obtained due to loss of sample in the subsequent liquid-gas transition.

Figure 3:
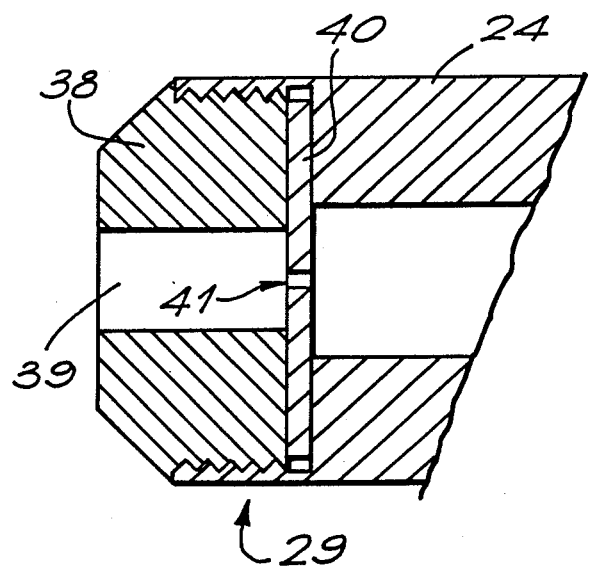
FIG. 3 shows the arrangement of part of the discharge ionization source shown in FIG. 2.

Referring next to FIG. 3, means 29 for reducing the pressure comprise a nozzle 38 which is threaded into the end of tube 24. Nozzle 38 contains a large (approximately 0.2 mm diameter) orifice 39 and secures a thin diaphragm 40 which contains a laser drilled pinhole 41, typically 2-5 micron diameter. This provides a very short non-viscous restriction across which substantially all the pressure reduction of the super-critical fluid takes place without any liquid-gas transitions. However, the volume of the connecting tubes 23–25 may in some cases result in an unacceptable loss in chromatographic resolution, and the presence of heated metallic surfaces may cause decomposition of certain samples. In such cases, the arrangement shown in FIG. 4 may be preferable.

Figure 4:
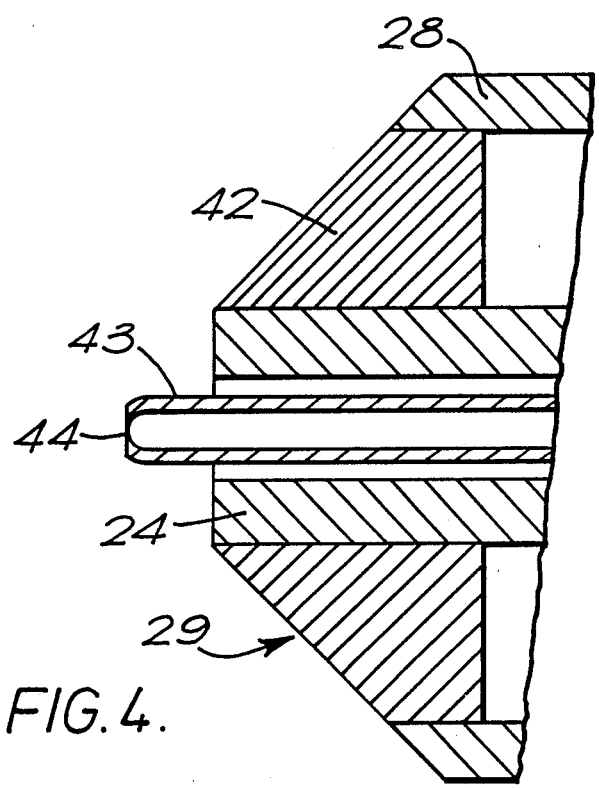
FIG. 4 shows an alternative preferred arrangement of part of the discharge ionization source shown in FIG. 2.

Referring next to FIG. 4, an alternative form of means 29 for reducing pressure comprises tube 28 which is sealed with a plug 42 into which narrow bore tube 24 is fitted in a vacuum tight manner. A length of silica capillary tube 43 (typically 0.1 mm diameter) is threaded through tube 24 so that the end extends beyond coupling 33 (FIG. 2) to a point where tube 24 is terminated. Capillary 43 extends beyond this end of tube 24 and is connected to a conventional SFC column by a suitable pipe fitting. A vacuum-tight seal is provided between the capillary 43 and the end of tube 24 by means of a drilled out pipe coupling through which capillary 43 passes without a break. Ferrules (typically PTFE) are fitted in this pipe coupling to seal the exterior of tube 24 (which terminates in the coupling) at one side and to seal the exterior of capillary 43 at the other side. In this way the SFC eluent contacts only silica surfaces as it passes from the column to the ionization chamber 9.

The end of capillary 43 which protrudes into ionization chamber 9 contains at least one small orifice (1–10 micron diameter) across which the bulk of the pressure drop takes place, as in the case of the diaphragm 40 in the FIG. 3 embodiment. The silica orifice may be made by drawing out capillary 43 into a tapered restriction, but it is preferable to seal the end of the tube and then grind it flat until a very small orifice 44 is formed, as shown in FIG. 4.

In the FIG. 4 embodiment the cathode electrode of the discharge is made tube 24 as in the FIG. 3 embodiment, so that it is adjacent to the orifice 44 in capillary 43. In this way the SFC eluent is expanded into the cathode dark space of the discharge according to the preferred form of the invention.

It will be appreciated that although the embodiments illustrated show a preferred form of the invention in which the cathode electrode of the discharge comprises means 29 for reducing pressure, this is not essential. A considerable improvement in the range of compounds which can be analyzed, in comparison with prior SFC mass spectrometers, is also obtained if the glow discharge 45 is struck between a remote cathode electrode and the ionization chamber 9, or even between two separate electrodes disposed in the chamber.

What is claimed is:

1. A mass spectrometer for the analysis of a sample in solution in a super-critical fluid, said spectrometer comprising:
   (a) means for reducing the pressure of said super-critical fluid solution and introducing at least some of the resulting sample-containing expanded fluid into an ionization chamber maintained substantially below atmospheric pressure;
   (b) means for maintaining within said ionization chamber a glow discharge whereby to produce ions characteristic of said sample;
   (c) means for extracting from said ionization chamber at least some of said ions, and
   (d) means for mass analyzing at least some of the said ions extracted by said means for extracting.

2. A mass spectrometer according to claim 1 comprising a super-critical fluid chromatograph and means for conducting super-critical fluid eluent therefrom to said means for reducing the pressure.

3. A mass spectrometer according to claim 1 in which said means for reducing the pressure is disposed in or adjacent to said ionization chamber and comprises a non-viscous restriction, wherethrough said super-critical fluid solution may be expanded into said ionization chamber without undergoing an intermediate liquid-gas transition.

4. A mass spectrometer according to claim 1 in which said means for reducing the pressure comprises a diaphragm provided with an orifice having an area between $1 \times 10^{-12}$ and $3 \times 10^{-11}$ m$^2$.

5. A mass spectrometer according to claim 1 in which said means for maintaining a glow discharge comprises at least two electrodes, at least one of which is provided by said means for reducing the pressure.

6. A mass spectrometer according to claim 1 in which said means for maintaining a glow discharge comprises at least two electrodes, at least one of which is disposed adjacent to said means for reducing the pressure.

7. A mass spectrometer according to claim 1 in which said means for extracting comprises a hollow conical member having a hole in its apex through which said ions may pass along a first axis to said means for mass analyzing, said conical member being disposed to protrude apex-first into said ionization chamber and said first axis being substantially perpendicular to a second axis along which said fluid enters said ionization chamber.

8. A mass spectrometer according to claim 7 in which the distance between said means for reducing the pressure and said first axis is between 3 and 6 mm.

9. A mass spectrometer according to claim 1 in which said means for maintaining a glow discharge comprises at least two electrodes, at least one of which comprises at least a part of the wall of said ionization chamber.

10. A mass spectrometer according to claim 1 in which said means for maintaining a glow discharge comprises at least one electrode maintained at a potential of several hundred volts more negative than the potential of said ionization chamber.

11. A mass spectrometer according to claim 1 in which at least said means for reducing the pressure is provided with heating means to prevent condensation during expansion of said super-critical fluid solution.

12. A mass spectrometer according to claim 1 further comprising means for introducing an additional gas into said ionization chamber.

13. A method of analyzing a sample in solution in a super-critical fluid, said method comprising the steps of:
   (a) reducing the pressure of said super-critical fluid solution and expanding at least some of said solution into the vapour phase;
   (b) admitting at least some of the resulting sample-containing expanded fluid into an ionization chamber maintained at sub-atmospheric pressure;
   (c) ionizing at least some of said sample by means of a glow discharge established in said ionization chamber to produce ions characteristic of said sample,
   (d) extracting from said ionization chamber and subsequently mass analyzing at least some of said ions.

14. A method according to claim 13 in which said super-critical fluid is expanded into a cathode dark space of said glow discharge.

15. A method according to claim 13 in which said super-critical fluid solution is expanded without causing a liquid-gas transition to occur.

* * * * *